(12) United States Patent
Hoshino et al.

(10) Patent No.: US 7,442,769 B2
(45) Date of Patent: Oct. 28, 2008

(54) ANTIFREEZE PROTEINS FROM BASIDIOMYCETES

(75) Inventors: Tamotsu Hoshino, Hokkaido (JP); Michiko Kiriaki, Hokkaido (JP); Sakae Tsuda, Hokkaido (JP); Satoru Ohgiya, Hokkaido (JP); Hidemasa Kondo, Hokkaido (JP); Yuji Yokota, Hokkaido (JP); Isao Yumoto, Hokkaido (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 11/272,067

(22) Filed: Nov. 14, 2005

(65) Prior Publication Data

US 2006/0068470 A1 Mar. 30, 2006

Related U.S. Application Data (62) Division of application No. 10/386,529, filed on Mar. 13, 2003, now abandoned.

(30) Foreign Application Priority Data

Mar. 15, 2002 (JP) ............................. 2002-072612
Mar. 5, 2003 (JP) ............................. 2003-57888

(51) Int. Cl.
 *C07K 1/00* (2006.01)
(52) U.S. Cl. ..................................... 530/350; 530/300

(58) Field of Classification Search ....................... None
See application file for complete search history.

(56) References Cited

U.S. PATENT DOCUMENTS 5,500,353 A * 3/1996 Smit et al. ................. 435/69.1

OTHER PUBLICATIONS

Seffernick et al. (J. Bacteriology, vol. 183, pp. 2405-2410, 2001).*
Wells (Biochemistry, vol. 29, pp. 8509-8517, 1990).*
Newsted W Jay et al: "A low molecular weight peptide from snow mold with epitopic homology to the winter flounder antifreeze protein." Biochemistry and Cell Biology, vol. 72, No. 3-4, 1994, pp. 152-156.
Snider Christopher S et al: "Role of ice nucleation and antifreeze activities in pathogenesis and growth of snow molds." Phytopathology, vol. 90, No. 4, Apr. 2000, pp. 354-361.
Schneider E F et al: "Saprophytic Behavior of Three Typhula-SPP on Winter Wheat Substrates" Canadian Journal of Plant Pathology, vol. 10, No. 4, 1988, pp. 289-296.
Wells, Biochemistry, vol. 29, pp. 8509-8517, 1990.
Seffernick, et al., J. Bacteriology, vol. 183, pp. 2405-2410, 2001.

* cited by examiner

*Primary Examiner*—Hope A Robinson
(74) *Attorney, Agent, or Firm*—Sughrue Mion, PLLC (57) ABSTRACT

The present invention provides antifreeze proteins produced by a basidiomycete. The antifreeze protein has a high antifreeze activity such as a thermal hysteresis activity or an ice-recrystallization inhibition activity.

4 Claims, 2 Drawing Sheets

ANTIFREEZE PROTEINS FROM BASIDIOMYCETES

This application is a divisional of application Ser. No. 10/386,529 filed Mar. 13, 2003, which is abandoned, which claims priority to Japanese Application No. 2002-072612, filed Mar. 15, 2002, and Japanese Application No. 2003-57888, filed Mar. 5, 2003, the entire disclosures of which are considered part of the disclosure of the accompanying divisional application and are hereby incorporated by reference.

FIELD OF THE INVENTION

The present invention relates to novel proteins originated from fungi. In particular, the present invention relates to antifreeze proteins excellent in antifreeze activity and useable as ice recrystallization inhibitors and cryopreservatives, and a method of preparing the same.

BACKGROUND OF THE INVENTION

A protein exhibiting an antifreeze effect on aqueous solutions is generally referred to as an antifreeze protein (AFP). Various antifreeze protein have been found in living organisms such as fish, insects, plants, fungi and bacteria which typically have adaptability to low temperature environments. It is know that all antifreeze proteins originated from fish and plants allow an ice nucleus to grow to an ice crystal having a bi-pyramid shape, just like a pair of triangular pyramids joined together at their bottom surfaces. This mechanism is explained as follows. Under usual conditions, upon generation of an ice nucleus in an aqueous solution, an ice crystal first grows to have a flat hexagonal plate shape. In this case, the ice crystal has a growth rate in the vertical direction 100 times lower than that in the plate plane direction. In contrast, when an antifreeze protein is present in the aqueous solution, the ice crystal gradually grows to the bi-pyramid-shaped ice crystal under restraint on its growth in the plate plane direction in such manner that a plate-shaped body is initially formed to provide a base plane, and a plurality of small plate-shaped bodies are sequentially piled up on both sides of the plate-shaped body in the vertical direction with respect to the base plane.

An antifreeze protein dissolved in an aqueous solution brings about an antifreeze effect on the aqueous solution, such as 1) thermal hysteresis, 2) ice-recrystallization inhibition, and 3) ice crystal shape control. While the water freezing point is generally equal to the ice melting point, an aqueous solution containing an antifreeze protein has a depressed water freezing point because the protein is bonded to an ice crystal to be formed. This phenomenon is referred to as "thermal hysteresis," and the difference between the melting point of the ice formed therein and the water freezing point is defined as "depression of freezing point." A greater depression of freezing point means a greater antifreeze effect. The ice crystal formed therein grows while absorbing water generated by sublimation or partial melting at a relatively high temperature of −10° C. or more. Inhibition of this phenomenon is defined as "ice-recrystallization inhibition." A higher ice-recrystallization-inhibition activity means a higher antifreeze effect. By taking advantage of the above properties of the antifreeze protein, the antifreeze protein has been proposed for use as an additive for ice cream apt to deteriorate in its flavor or taste due to attachment/recrystallization of water molecules in ambient air caused by cold insulation, or as a cryopreservative for cells and organs. The antifreeze protein is also expected to function as an effective additive for eliminating clogging of pipelines due to ice recrystallization in a system using ice slurry, such as cryogenic supply systems or cryogenic storage systems.

However, it is difficult to assure a large, stable supply of most of the known antifreeze proteins originated from plants and animals. Therefore, recombinant gene technology has been used to produce some antifreeze proteins originated from fish or insects, and to make the proteins more stable. However, antifreeze proteins produced by recombinant methods have not been used in foods for human consumption because of consumer opposition to gene-altered products. While some antifreeze proteins have been successfully purified from bacteria, they are not suitable for human consumption due to the properties related to their bacterial origin, and due to insufficient stability. While it has been reported that some antifreeze proteins exist in basidiomycetes, which are widely utilized for human consumption, no antifreeze protein has been isolated/purified therefrom.

While various attempts have heretofore been made to put natural antifreeze proteins mainly originated from plants or fish to practical use as a quality improving agent for frozen foods such as ice cream, as a cryopreservative for cells, and as an additive for cryogenic supply systems or cryogenic storage systems, no practical application has been achieved due to instability in activity of the conventional antifreeze proteins and the resulting need for using them in large quantities to bring about desired functions in view of their poor stability.

SUMMARY OF THE INVENTION

It is therefore an object of the present invention to provide an antifreeze protein having a high antifreeze activity, and capable of being preparing in large quantities at a low cost.

In order to achieve this object, through various research the present inventors have found that basidiomycetes, such as *Typhula ishikariensis*, produce novel proteins having a high antifreeze activity, and that antifreeze proteins meeting the above objects can be isolated and purified therefrom. Based on this knowledge, the inventors have accomplished the present invention relating to novel proteins which are produced by basidiomycetes and secreted out of cells thereof, and a method of preparing the antifreeze proteins.

Specifically, according to a first aspect of the present invention, there is provided antifreeze proteins which are produced by basidiomycetes.

In the first aspect of the present invention, the basidiomycetes may be a fungi belonging to the order Aphyllophorales. The fungi belonging to the order Aphyllophorales may be a fungi belonging to the family Ramariaceae.

Alternatively, the basidiomycetes may be a fungi belonging to the order Agaricales. The fungi belonging to the order Agaricales may belong to the family Coprinaceae or the family Tricholomataceae.

Preferably, the basidiomycetes is *Typhula ishikariensis*.

The antifreeze proteins according to the first aspect of the present invention have the ability to depress the freezing point of an aqueous solution.

The antifreeze proteins according to the first aspect of the present invention have an N-terminal amino acid sequence selected from the group consisting of:

(SEQ ID NO: 1)
Ala-Gly-Pro-Ser-Ala-Val-Ala-Gly-Leu-Thr-Ala-Gly-
Asn-Tyr-Ala-Ile-Leu-Ala-Ser-Thr,

-continued

```
                                            (SEQ ID NO: 2)
Ala-Gly-Pro-Ser-Ala-Val-Pro-Leu-Gly-Thr-Ala-Gly-
Asn-Tyr-Val-Ile-Leu-Ala-Ser-Thr, (SEQ ID NO: 3)
Ala-Gly-Pro-Thr-Ala-Val-Pro-Leu-Gly-Thr-Ala-Gly-
Asn-Tyr-Ala-Ile-Leu-Ala-Ser-Thr, (SEQ ID NO: 4)
Ala-Gly-Pro-Ser-Ala-Val-Pro-Leu-Gly-Thr-Ala-Gly-
Asn-Tyr-Ala-Ile-Leu-Ala-Ser-Thr, (SEQ ID NO: 5)
Ala-Gly-Pro-Thr-Ala-Val-Asn-Leu-Gly-Thr-Ala-Lys-
Asn-Tyr-Ala-Ile-Leu-Thr-Lys-Ala, (SEQ ID NO: 6)
Ala-Gly-Pro-Thr-Ala-Val-Asn-Leu-Gly-Thr-Ala-Lys-
Thr-Tyr-Ala-Ile-Leu-Thr-Lys-Ala, (SEQ ID NO: 7)
Ala-Gly-Pro-Thr-Ala-Val-Asn-Leu-Gly-Thr-Ala-Lys-
Asn-Tyr-Ala-Ile-Leu-Thr-Lys-Thr,
and
``` an N-terminal amino acid sequence substantially homologous to any one of SEQ ID NOS: 1 to 7.

According to a second aspect of the present invention, there is provided a polypeptide comprising an N-terminal amino acid sequence selected from the group consisting of:

```
                                            (SEQ ID NO: 1)
Ala-Gly-Pro-Ser-Ala-Val-Ala-Gly-Leu-Thr-Ala-Gly-
Asn-Tyr-Ala-Ile-Leu-Ala-Ser-Thr, (SEQ ID NO: 2)
Ala-Gly-Pro-Ser-Ala-Val-Pro-Leu-Gly-Thr-Ala-Gly-
Asn-Tyr-Val-Ile-Leu-Ala-Ser-Thr, (SEQ ID NO: 3)
Ala-Gly-Pro-Thr-Ala-Val-Pro-Leu-Gly-Thr-Ala-Gly-
Asn-Tyr-Ala-Ile-Leu-Ala-Ser-Thr, (SEQ ID NO: 4)
Ala-Gly-Pro-Ser-Ala-Val-Pro-Leu-Gly-Thr-Ala-Gly-
Asn-Tyr-Ala-Ile-Leu-Ala-Ser-Thr, (SEQ ID NO: 5)
Ala-Gly-Pro-Thr-Ala-Val-Asn-Leu-Gly-Thr-Ala-Lys-
Asn-Tyr-Ala-Ile-Leu-Thr-Lys-Ala, (SEQ ID NO: 6)
Ala-Gly-Pro-Thr-Ala-Val-Asn-Leu-Gly-Thr-Ala-Lys-
Thr-Tyr-Ala-Ile-Leu-Thr-Lys-Ala, (SEQ ID NO: 7)
Ala-Gly-Pro-Thr-Ala-Val-Asn-Leu-Gly-Thr-Ala-Lys-
Asn-Tyr-Ala-Ile-Leu-Thr-Lys-Thr,
and
``` an N-terminal amino acid sequence substantially homologous to any one of SEQ ID NOS: 1 to 7. This polypeptide has a molecular mass of 15 to 30 kDa, and the ability to depress the freezing point of an aqueous solution.

According to a third aspect of the present invention, there is provided a polypeptide comprising the following amino acid sequence (a) or (b):

an amino acid sequence shown in any one of SEQ ID NOS: 9, 11, 13, 15, 17, 19 and 21;

an amino acid sequence having one or more amino acid deletions, substitutions or additions relative to an amino acid sequence shown in any one of SEQ ID NOS: 9, 11, 13, 15, 17, 19 and 21. This polypeptide has the ability to depress the freezing point of an aqueous solution.

According to a fourth aspect of the present invention, there is provided a polynucleotide encoding the following polypeptide (a) or (b):

a polypeptide comprising an amino acid sequence shown in any one of SEQ ID NOS: 9, 11, 13, 15, 17, 19 and 21;

a polypeptide comprising an amino acid sequence having one or more amino acid deletions, substitutions or additions relative to an amino acid sequence shown in any one of SEQ ID NOS: 9, 11, 13, 15, 17, 19 and 21. This polypeptide (a) or (b) has the ability to depress the freezing point of an aqueous solution.

According to a fifth aspect of the present invention, there is provided a polynucleotide comprising the following polynucleotide sequence (a) or (b):

a polynucleotide comprising a base sequence shown in any one of SEQ ID NOS: 8, 10, 12, 14, 16, 18 and 20;

a polynucleotide which hybridizes under stringent conditions with a polynucleotide comprising a base sequence complementary to a polynucleotide consisting of all or a part of a base sequence shown in any one of SEQ ID NOS: 8, 10, 12, 14, 16, 18 and 20. This polynucleotide (a) or (b) encodes a polypeptide which has the ability to depress the freezing point of an aqueous solution.

According to a six aspect of the present invention, there is provided a recombinant vector containing the polynucleotide set forth in the fourth or fifth aspect of the present invention.

According to a seventh aspect of the present invention, there is provided a transformant containing the recombinant vector set forth in the sixth aspect of the present invention.

According to an eighth aspect of the present invention, there is provided a method of preparing an antifreeze protein, which comprises culturing the transformant set forth in the seventh aspect of the present invention, and collecting the antifreeze protein from the resulting culture.

According to a ninth aspect of the present invention, there is provided an antifreezing agent containing the protein set forth in any one of the first to third aspects of the present invention.

According to a tenth aspect of the present invention, there is provided an antibody which reacts specifically with the protein set forth in any one of the first to third aspects of the present invention.

According to an eleventh aspect of the present invention, there is provided a polypeptide-antibody complex comprising a polypeptide and an antibody bound to the polypeptide through an immune reaction. The antibody specifically recognizes and binds to an epitope of a protein or polypeptide set forth in any one of the first to third aspects of the present invention. The polypeptide-antibody complex has the ability to depress the freezing point of an aqueous solution.

According to a twelfth aspect of the present invention, there is provided a method of preparing an antifreeze protein, which comprises culturing a basidiomycete capable of producing the antifreeze protein, under low temperature, and collecting the produced antifreeze protein from the resulting cultured solution.

DESCRIPTION OF THE PREFERRED EMBODIMENT

The term "antifreeze protein" herein has an ordinary meaning commonly recognized in the art, and means a protein having an activity that inhibits ice-crystal growth.

An antifreeze protein according to one embodiment of the present invention is contained in an extract from basidiomycetes. A basidiomycete to be used in the present invention may be any strain capable of producing a protein having an antifreeze activity, preferably a strain capable of growing at a low temperature of 4° C. or less.

Preferably, the basidiomycetes belong to Aphyllophorales or Agaricales. The basidiomycetes belonging to Aphyllophorales include fungi belonging to Cantharellaceae, Polyporaceae, Ganodermataceae, Hydnaceae, Schizophyllaceae, Coniophoraceae, Ramariaceae, Stereaceae, and Thelephoraceae. The basidiomycetes belonging to Agaricales include fungi belonging to Hygrophoraceae, Tricholomataceae, Amanitaceae, Agaricaceae, Coprinaceae, Strophariaceae, Cortinariaceae, Boletaceae, and Russulaceae.

Preferably, the basidiomycetes include: fungi belonging to Aphyllophorales-Ramariaceae-*Typhula*, such as *Typhula ishikariensis, T. incarnata* or *T. phacorrhiza*; fungi belonging to Agaricales-Coprinaceae-*Coprinus* (*Coprinus psychromorbidus*); and fungi belonging to Agaricales-Tricholomataceae-*Flammulina*, such as *Flammulina velutipes*. More preferably, the basidiomycetes are fungi belonging to *Typhula* and *Coprinus*. The *Typhula ishikariensis* BRB strain and the *Coprinus psychromorbidus* CCFC006721 strain may be used as particularly preferable basidiomycetes.

The *Typhula ishikariensis* BRB strain is a new strain isolated from the natural environment. The *Typhula ishikariensis* BRB strain exhibits the following microbiological properties.

One or several fruit-bodies each having a length of 0.5 cm are generated from each of the sclerotia. The fruit body includes a cylindrical club-shaped top portion having a length of 0.2-0.5 cm (about 3 cm under artificial conditions), a diameter of 0.5-2.0 mm, and a color of white or approximate-white which will change to light champagne after maturation. Thus, the top portion is obviously distinguishable from the stem portion of the fruit body. A basidium has a club shape and bears 4 spores. Each of the spores has a flat shape of about 10×5 μm. The sclerotium has a spherical, oval or indefinite shape having a diameter of 0.5-3 mm, and a dark-brown wet body which will change to black when dried. In view of the above microbiological properties, the above strain can be classified into *Typhula ishikariensis* on the basis of "Nihonkingakkaiho," Vol. 2, Basidiomycetes No. 4" as a references of classification/identification. This strain "*Typhula ishikariensis* BRB" was deposited as deposit number FERM P-18741 in International Patent Organism Depositary, National Institute of Advanced Industrial Science and Technology, Tsukuba Central 6, 1-1-1 Higashi, Tsukuba, Ibaraki, Japan (zip code: 305-5466) on Feb. 27, 2002.

The *Coprinus psychromorbidus* CCFC006721 strain was deposited as deposit number CCFC006721 in the Canadian Collection of Fungal Cultures, Agriculture and Agri-Food Canada, Rm. 1015, K. W. Neatby Bldg., Ottawa, Ontario, K1A 0C6 CANADA.

The antifreeze proteins of the present invention can be prepared by culturing a specific basidiomycete in a culture medium and collecting an antifreeze protein from the resulting culture solution. The culture medium to be used for culturing the basidiomycete is not limited to a specific form, but any suitable natural or synthetic culture medium containing an appropriate amount of nutritional elements required for activating the strain, such as carbon source, nitrogen source or inorganic substance may be used. For example, the medium may include a potato-dextrose medium and a cornmeal medium which are typically used for culturing filamentous fungi. The carbon source for use in the synthetic medium may include soluble starch, glucose and maltose. The nitrogen source may include a nitrogen-containing natural product such as peptones, yeast extracts or meat extracts, and a nitrogen-containing inorganic compound such as sodium nitrate or ammonium chloride. The inorganic substance may include potassium phosphate, sodium phosphate, magnesium sulfate, calcium chloride and ferric chloride. The culturing method typically includes, but not limited to, a shaking culturing method, an aeration/agitation culturing method and a two-step culturing method. The culturing temperature is set at any low temperature, preferably in the range of 0 to 15° C., more preferably 0° C. or less. Alternatively, cells may be sufficiently proliferated at an optimal growth temperature, and then transferred into another medium to culture them at 0° C. or less. A culturing period is typically 1 to 7 weeks.

The antifreeze proteins of the present invention can be purified through any conventional purification method commonly used in the art. The cultivated cells may be separated from the culture medium, for example, through centrifugation, filtration or ultrafiltration. The antifreeze proteins contained in the supernatant of a culture solution resulting from the separation of the cells can be isolated/purified through a salting-out method using ammonium sulfate or sodium sulfate, an organic-solvent precipitation method using acetone or ethanol, a column chromatography method using a cation exchanger (e.g. CM, S, SP) or an anion exchanger (e.g. DEAE, Q, QAE), or a gel filtration method using agarose derivatives.

The inventors also isolated antifreeze proteins, and a polynucleotides encoding the proteins, from the strain "*Typhula ishikariensis* BRB." The polynucleotides encoding the antifreeze proteins can be isolated through any suitable method commonly used in the art (see, for example, WO 00/188045).

The antifreeze proteins of the present invention may comprise an amino acid sequence shown in any one of SEQ ID NOS: 9, 11, 13, 15, 17, 19 and 21, and the polynucleotides encoding the antifreeze proteins of the present invention may comprise a base sequence shown in any one of SEQ ID NOS: 8, 10, 12, 14, 16, 18 and 20. As long as the proteins comprising the above amino acid sequences have the ability to depress the freezing point of an aqueous solution, the amino acid sequences may include a variation or mutation such as one or more amino acid deletions, substitutions or additions.

Thus, the antifreeze proteins of the present invention include those proteins substantially homologous to any one of the amino acid sequences shown in SEQ ID NOS: 9, 11, 13, 15, 17, 19 and 21.

The term "substantially homologous" as used throughout means that two polypeptides have at least 80%, preferably 90% or more, more preferably 95 to 100%, common amino acids.

For example, in the amino acid sequences shown in any one of SEQ ID NOS: 9, 11, 13, 15, 17, 19 and 21, one amino acid, preferably 10 to 20 amino acids, more preferably 5 to 10 amino acids, may be deleted therefrom or substituted with different amino acids. Alternatively, or in addition, one amino acid, preferably 10 to 20 amino acids, more preferably 5 to 10 amino acids may be added to the amino acid sequence shown in any one of SEQ ID NOS: 9, 11, 13, 15, 17, 19 and 21. The polynucleotides encoding the antifreeze proteins of the present invention also include polynucleotides which hybridizes under stringent conditions with a polynucleotide comprising a base sequence complementary to a polynucleotide consisting of all or a part of the base sequence shown in any one of SEQ ID NOS: 8, 10, 12, 14, 16, 18 and 20, and encodes a protein having the ability to depress the freezing point of an aqueous solution. The term "stringent conditions" herein means conditions under which a specific hybrid is formed without formation of a non-specific hybrids, or conditions under which a polynucleotide having a high homology (homology: 90% or more, preferably 95% or more) to the polynucleotide encoding the antifreeze protein is hybridized. More specifically, such conditions can be achieved by performing hybridization at 42 to 68° C. under the presence of 0.5 to 1 M NaCl, and then rinsing a filter at room temperature to 68° C. by using a 0.1 to 2 times concentration of SSC (saline sodium citrate) solution. Preferably, stringent conditions mean hybridization at 68° C. in the presence of 1 M NaCl, and washing at 68° C. in a 2× concentration of SSC solution.

The term "part of the base sequence" herein means a base sequence of a polynucleotide including a part of the base sequence of the above polynucleotide encoding the antifreeze protein, wherein the polynucleotide encodes a protein having the ability to depress the freezing point of an aqueous solution. The "part of the base sequence" has a length sufficient to be hybridized under stringent conditions. For example, it is constructed by at least 10 bases, preferably at least 50 bases, more preferably 200 bases.

A mutation can be introduced in the polynucleotide through a conventional technique, such as a Kunkel method or a Gapped duplex method, or a method based on these methods, for example, by using a mutation-introducing kit utilizing a site-specific mutation inducing method (e.g. Mutan-K available from TAKARA, MUTAN-G available from TAKARA) or LA PCR in vitro Mutagenesis series kits available from TAKARA. A polynucleotide having a base sequence produced through the above technique can be produced through a chemical synthesis method or a PCR method using a chromosomal DNA as a template, or by using a polynucleotide fragment having the base sequence as a probe to obtain the polynucleotide of the present invention.

The antifreeze proteins may also be obtained by preparing a recombinant vector containing the polynucleotide encoding a antifreeze protein of the present invention, and culturing a transformant having the recombinant vector introduced therein. The recombinant vector of the present invention can be obtained by linking all or a part of a polynucleotide of the present invention to a suitable vector. The transformant of the present invention can be obtained by introducing the recombinant vector of the present invention into a host to allow a polynucleotide of the present invention to be expressed. The term "part of the polynucleotide" herein means a part of a polynucleotide encoding a antifreeze protein capable of expressing a antifreeze protein of the present invention when it is introduced into a host.

The recombinant vector used in the present invention is not limited to a specific type, but may be any suitable vector capable of cloning in host cells, such as plasmid, shuttle vector, phage or helper plasmid. If the vector itself has no clonability, a DNA fragment capable of providing clonability when it is inserted into the chromosome of a host may be used in combination therewith.

The plasmid may be, but is not limited to, a plasmid originated from *Escherichia coli* (e.g. pBR322, pBR325, pUC118, pUC119, pUC18, pUC19 or pBluescript), a plasmid originated from *Bacillus subtilis* (e.g. pUB110 or pTP5), and a plasmid originated from yeast (e.g. Yeps such as Yep 13, or Ycps such as Ycp 50). The phage may be, but is not limited to, λ phage (Charon4A, Charon21A, EMBL3, EMBL4, λ gt 10, λ gt 11, or λ gt ZAP). An animal virus vector such as retrovirus or vaccinia virus, or an insect virus vector such as Baculovirus may also be used in combination.

The host is not limited to a specific type, but may include: bacteria belonging to the *Ralstonia* genus such as *Ralstonia eutropha*; bacteria belonging to the *Pseudomonas* genus such as *Pseudomonas putido*; bacteria belonging to the *Bacillus* genus such as *Bacillus subtilis*; bacteria belonging to the *Escherichia* genus such as *Escherichia coli*; yeast belonging to the *Saccharomyces* genus such as *Saccharomyces cerevisiae*; yeast belonging to the *Candida* genus such as *Candida maltosa*; animal cells such as COS cells, CHO cells, mice L cells, rat GH3 or human FL cells; and insect cells such as SF9 cells.

When a bacterium such as *Escherichia coli* is used as a host, it is preferable that the recombinant vector can exist independently in the host, and comprises a promoter, a polynucleotide of the present invention and a transcription termination sequence. The promoter may be any suitable type capable of being expressed in the host, for example, a promoter originated from *Escherichia coli* or phage, such as a trp promoter, Lac promoter, $P_L$ promoter, $P_E$ promoter or T7 promoter. The method used to introduce the recombinant vector into cells may be, but is not limited to, a method using calcium ions [Current Protocols in Molecular Biology, 1, 181 (1994)] or an electroporation method.

When yeast is used as a host, the expression vector may be YEp13 or YCp50. In this case, a promoter may include a gal 1 prompter, gal 10 promoter, heat-shock protein promoter, and GAP promoter. The method used to introduce the recombinant vector into yeast may be, but is not limited to, an electroporation method, a Spheroplast method [Proc. Natl. Sci. USA, 84, 192, 9-1933 (1978)] or a lithium acetate method [J. Bacteriol., 153, 163-168 (1983)].

An antifreeze protein of the present invention is obtained by culturing a transformant of the present invention in a culture medium to produce and accumulate an antifreeze protein in the resulting culture (culture cells or culture supernatant), and collecting the antifreeze protein from the culture. A transformant of the present invention is cultured in a culture medium through a conventional method for culturing a host. A culture medium for culturing the transformant obtained by using bacteria such as *Escherichia coli* as the host includes a complete medium such as LB medium, and a synthetic medium such as M9 medium. The transformant is aerobically cultured at a temperature of 25 to 37° C. for 1 to 72 hours to accumulate the antifreeze protein in the cells, and the accumulated antifreeze protein is collected. During culturing, the pH value in the culture medium is maintained at about 7. The pH value is adjusted using an inorganic acid, organic acid or alkaline solution. The collected antifreeze protein can be purified in the same manner as that described above.

The roughly purified antifreeze proteins or the entirely purified antifreeze proteins obtained through the above process may be used in a liquid form by adding thereto a stabilizer such as glycerol, sucrose, or ethylene glycol, or may be used in a powder form by drying it, for example, through a spray drying method or a freeze-drying method.

As described above, the antifreeze proteins of the present invention can be collected from a culture solution obtained by culturing a specific basidiomycete or a transformant comprising a polynucleotide encoding a antifreeze protein. Thus, the basidiomycete strain or the transformant can be readily cultured on a large scale by using an inexpensive medium to prepare the desired antifreeze protein in large quantities at a low cost.

The present invention also includes a polypeptide-antibody complex comprising a polypeptide and an antibody bound to the polypeptide through an immune reaction. The complex has the ability to depress the freezing point of an aqueous solution. Such a protein can be prepared by immunizing an animal with the antifreeze protein of the present invention and collecting the resulting antibody (see, for example, WO 00/188045).

The term "antifreeze activity" herein means an activity of inhibiting ice-crystal growth. The antifreeze activity can be determine, for example, by observing the growth process of ice crystals in a solution containing an antifreeze protein, and the shape of the ice crystals being formed, or by measuring the freezing point depression of the solution with an osmometer using a freezing point depression method. More specifically, the presence of the antifreeze activity in a specific protein can be determine by identifying through microscopic observations the fact that no ice-crystal growth is generated in a solution containing the specific protein, or that an ice crystal formed in the solution containing the specific protein has an indented shape, for example, a chipped-stone-tool shape or a star shape. The level of the antifreeze activity of the protein can also be determined in proportion to the freezing point depression in the solution.

With respect to a first sample containing an antifreeze protein of the present invention originated from a specific basidiomycete and a second sample containing a conventional antifreeze protein originated from fish, the growth process of an ice-crystal, the shape of the formed ice crystal, and the freezing point depressions were experimentally determined in both the samples. As a result, it was verified that the ice crystal shape of an antifreeze protein of the present invention originating from the basidiomycete was different from that of the conventional high-activity-type antifreeze protein originated from fish, and the solution obtained from the first sample had a freezing point depression about 1.3 times greater than that obtained from the second sample. That is, the results show that an antifreeze protein of the present invention has an antifreeze activity about 1.3 times greater than that of the conventional antifreeze protein originated from fish.

A liquefied or powdered antifreeze protein obtained through the method of the present invention is excellent in antifreeze activity and productivity, and can be advantageously used as a quality-improving agent for frozen foods, a cryopreservative for cells, and an additive for cryogenic supply systems or cryogenic storage systems. The proteins of the present invention can also be used to prepare an antifreezing agent. In the present invention, plural kinds of proteins can be prepared, and mixed them together to form a complex of antifreeze proteins. The extract from a basidiomycete capable of producing an antifreeze protein also has an antifreeze activity usable directly for the above applications.

All publications, patents and patent application cited herein are incorporated herein by reference in their entirety.

EXAMPLE

While the present invention will be described in more detail in conjunction with the following Example, the invention is not limited thereto.

Example 1

Preparation of Antifreeze Proteins Originated from *Typhula ishikariensis*

1 L of Potato-Dextrose liquid medium (available from Difco) was put in an Erlenmeyer flask having a volume of 3 L, and subjected to autoclave sterilization at 121° C. for 15 minutes. The *Typhula ishikariensis* BRB strain (Deposit No: FERM P-18741) as a spawn was inoculated into the medium, and cultured at −1° C. for 1 month to obtain a culture solution. The culture solution was centrifugalized, and the obtained supernatant was dialyzed. Then, the dialyzed solution was fractionated through Q- and S-Bio-Gel column chromatography to obtain five kinds of purified protein samples. The obtained proteins had the following properties.

Through dodecyl sodium sulfate-polyacrylamide gel electrophoresis, all of the molecular masses of the proteins were in the range of 15 to 30 kDa, more specifically about 22 kDa. Through a gel filtration method and a dynamic light scattering method, it was also verified that each of the proteins was a monomer. Each of the N-terminal sequences of the proteins was determined through an Edman method. The following four kinds of sequences were determined:

```
                                          (SEQ ID NO: 1)
Ala-Gly-Pro-Ser-Ala-Val-Ala-Gly-Leu-Thr-Ala-Gly-
Asn-Tyr-Ala-Ile-Leu-Ala-Ser-Thr, (SEQ ID NO: 2)
Ala-Gly-Pro-Ser-Ala-Val-Pro-Leu-Gly-Thr-Ala-Gly-
Asn-Tyr-Val-Ile-Leu-Ala-Ser-Thr, (SEQ ID NO: 3)
Ala-Gly-Pro-Thr-Ala-Val-Pro-Leu-Gly-Thr-Ala-Gly-
Asn-Tyr-Ala-Ile-Leu-Ala-Ser-Thr,
and (SEQ ID NO: 4)
Ala-Gly-Pro-Ser-Ala-Val-Pro-Leu-Gly-Thr-Ala-Gly-
Asn-Tyr-Ala-Ile-Leu-Ala-Ser-Thr.
```

By checking with the Protein Sequence Database, it was verified that all of the proteins were novel. It is also intended that any proteins comprising an N-terminal amino acid sequence substantially homologous to either one of the above four kinds of N-terminal amino acid sequences are encompassed within the scope of the present invention. The term "substantially homologous" herein means that two polypeptides have at least 80%, preferably 90% or more, more preferably 95 to 100%, common amino acids. The N-terminal amino acid sequence of the remaining one of the proteins could not be determined through the Edman method, likely because it includes some kind of modification.

Example 2

Preparation of Antifreeze Proteins Originated from *Coprinus psychromorbidus*

1 L of Potato-Dextrose liquid medium (available from Difco) was put in an Erlenmeyer flask having a volume of 3 L, and subjected to autoclave sterilization at 121° C. for 15 minutes. The *Coprinus psychromorbidus* CCFC006721 strain as a spawn was inoculated into the medium, and cultured at −1° C. for 1 month to obtain a culture solution. The culture solution was centrifugalized, and the obtained supernatant was dialyzed. Then, the dialyzed solution was fractionated through Q- and S-Bio-Gel column chromatography to obtain three kinds of purified protein samples. The obtained proteins had the following properties.

Through dodecyl sodium sulfate-polyacrylamide gel electrophoresis, all of the molecular masses of the proteins were in the range of 15 to 30 kDa, more specifically about 23 kDa. Through a gel filtration method, it was also verified that each of the proteins was a monomer. Each of the N-terminal sequences of the proteins was determined through an Edman method. The following three kinds of sequences were determined:

```
                                         (SEQ ID NO: 5)
Ala-Gly-Pro-Thr-Ala-Val-Asn-Leu-Gly-Thr-Ala-Lys-
Asn-Tyr-Ala-Ile-Leu-Thr-Lys-Ala;

(SEQ ID NO: 6)
Ala-Gly-Pro-Thr-Ala-Val-Asn-Leu-Gly-Thr-Ala-Lys-
Thr-Tyr-Ala-Ile-Leu-Thr-Lys-Ala;
and (SEQ ID NO: 7)
Ala-Gly-Pro-Thr-Ala-Val-Asn-Leu-Gly-Thr-Ala-Lys-
Asn-Tyr-Ala-Ile-Leu-Thr-Lys-Thr.
```

By checking with the Protein Sequence Database, it was verified that all of the proteins were novel. It is also intended that any proteins comprising an N-terminal amino acid sequence substantially homologous to either one of the above three kinds of N-terminal amino acid sequences are encompassed within the scope of the present invention. The term "substantially homologous" herein means that two polypeptides they have at least 80%, preferably 90% or more, more preferably 95 to 100%, common amino acids.

Example 3

Preparation of Anti-*Typhula ishikariensis*-Originated Antifreeze Protein Antibodies A solution having 10 mg of a *Typhula* ishikariensis-originated antifreeze protein (selected from the polypeptides of SEQ ID NOS:1-3) dissolved therein was added to 1 ml of 1 mM sodium acetate buffer solution (pH 4.0), and the obtained solution was stirred at room temperature for three hours to prepare an antigen solution. The antigen solution was stirred in a syringe together with Freund's complete adjuvant (FCA) to form an emulsion, and a rabbit (Japanese white) was immunized with the emulsion. Subsequently, the rabbit was immunized at two-week intervals four times total. On and after the 2nd immunization, Freund's incomplete adjuvant was used instead of the FCA. A small amount of blood sample was taken from the immunized rabbit, and the increase of antibody value (500 ELISA-units/ml) was confirmed through a dot plot analysis using purified antifreeze protein from *Typhula ishikariensis*. Then, a large blood sample was taken from the rabbit. The blood sample was left at room temperature for 3.5 hours, and then left in a frigidarium for 48 hours to form a blood clot. Then, the blood clot was centrifuged at 3000 g to obtain blood serum. The obtained serum was stored at 4° C., and used as the source of the antibody.

Culture solutions of different basidiomycetes species were cultured at −1° C. for one month and were used as samples for checking the specificity of the immune reaction using the antibody. Each of the samples were individually subjected to dodecyl sodium sulfate-polyacrylamide gel electrophoresis, and then the ability of the antifreeze protein in the individual samples to be recognized by the antibody was checked though protein staining and western blotting. As a result, it was verified that antifreeze proteins in samples originated from *T. incarnata*, *T. phacorrhiza*, *Coprinus psychronlorbidus*, and *Flammulina velutipes* could each be detected by the antibody produced using the *Typhula ishikariensis* antifreeze protein as an immunogen.

Example 4

Measurement of Antifreeze Activity

1. Observation of Ice-Crystal Growth

Figure 1:
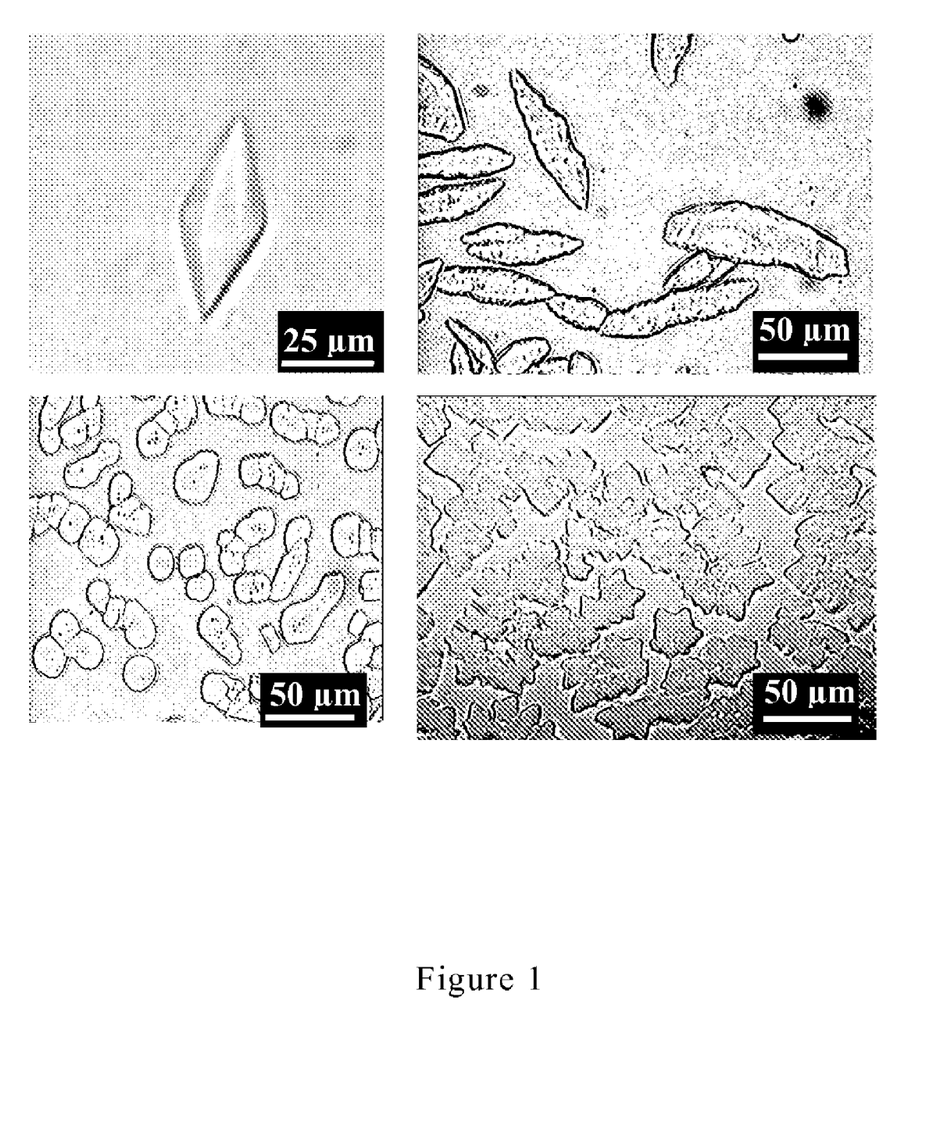
FIG. 1 includes pictures of respective ice crystals formed in a sample containing an antifreeze protein originated from fish (Type III) (A), a sample containing an antifreeze protein originated from *Typhula ishikariensis* (B), a *Pleurotus ostrea-* tus culture solution (C) and a *Flammulina velutipes* culture solution (D), each subjected to a low temperature treatment. An ice crystal having a typical bi-pyramidal structure is formed in the sample containing the antifreeze protein originated from fish, and ice crystals having different indented shapes, specifically a chipped-stone-tool shape, and a star shape, are formed in the samples containing the antifreeze protein originated from *Typhula ishikariensis* and the *Flammulina velutipes* culture solution, respectively. A spherical ice crystal is formed in the *Pleurotus ostreatus* culture solution.

Both a conventional fish-originated antifreeze protein (Type III) and the *Typhula ishikariensis* BRB strain-originated antifreeze protein prepared in Example 1 (corresponding to SEQ ID NO:3) were dissolved at a concentration of 0.25 mg/ml in 0.1 M ammonium hydrogencarbonate buffer solution (pH 7.9) to form corresponding samples. 3 µl of each of the samples were placed on a first cover glass of 1.6 mm diameter having a washer of 1.2 mm diameter and 0.8 mm thickness attached thereto with manicure, and then a second cover glass of 1.25 mm diameter was attached to the washer with manicure to cover the first cover glass. This measuring cell was placed on a refrigerating stage mounted on a microscope, and covered with a cover slip. The refrigerating stage was connected to a refrigerating system, and the temperature of the stage was controlled by a controller of the refrigerating system. The sample in the measuring cell was chilled down to −25° C. (−10° C./minute), and frozen. Then, the sample was heated to melt the ice formed there within, leaving only one ice nucleus. The sample was gradually chilled (−0.05° C./minute), and the ice-crystal growth in the sample was recorded by a highly-sensitive CCD camera system and a video recorder (see FIG. 1). While a bi-pyramidal-shaped ice crystal was formed in the sample containing the fish-originated antifreeze protein, a chipped-stone-tool-shaped ice crystal was formed in the sample containing the *Typhula ishikariensis*-originated antifreeze protein.

In observations of the *Coprinus psychromorbidus*-originated antifreeze protein obtained in EXAMPLE 2 (corresponding to SEQ ID NO:7), the formation of chipped-stone-tool-shaped ice crystal was also confirmed. Further, respective samples of a *Flammulina velutipes* culture solution and a *Pleurotus ostreatus* culture solution each subjected to a low temperature treatment were observed in the same way. As a result, it was verified that a star-shaped ice crystal was formed in the *Flammulina velutipes* culture solution, and a spherical ice crystal was formed in the *Pleurotus ostreatus* culture solution.

No ice-crystal growth was observed in the samples containing the *Typhula ishikariensis*-originated antifreeze protein, the *Coprinus psychroinorbidus*-originated antifreeze protein, and the *Flammulina velutipes* culture solution, even after they were kept at −5° C. for 1 hour. In contrast, a specific ice-crystal growth was observed in the sample of the *Pleurotus ostreatus* culture solution.

2. Measurement of Freezing Point

Figure 2:
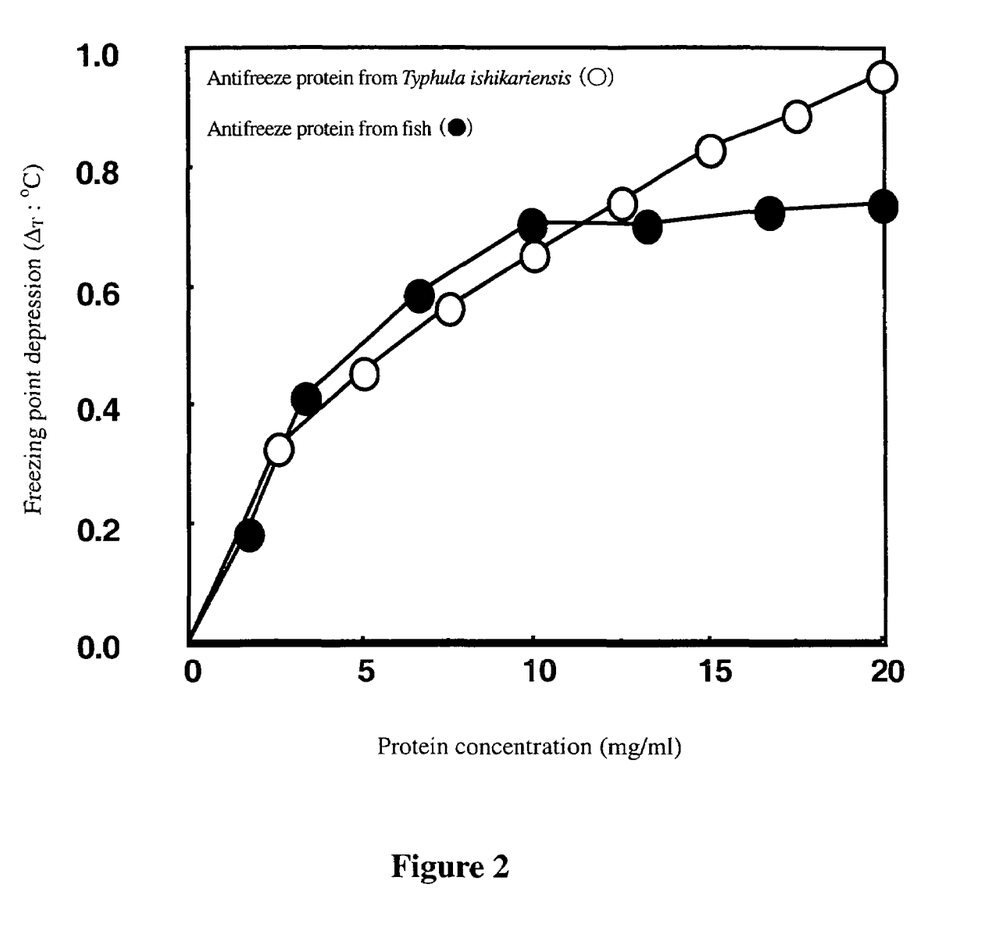
FIG. 2 is a graphical representation of the freezing point depressions in respective solutions containing the antifreeze protein originated from *Typhula ishikariensis* and the antifreeze protein originated from fish (Type III).

Both a fish-originated antifreeze protein (Type III) and the *Typhula ishikariensis* strain-originated antifreeze protein prepared in Example 1 (corresponding to SEQ ID NO:3) was dissolved at various concentrations in 0.1 M ammonium hydrogencarbonate buffer solution (pH 7.9) to form corresponding samples. With respect to 50 µl of each of the samples, a total osmotic pressure was measured with an osmometer through a freezing point depression method, and a freezing point was calculated in accordance with the measured total osmotic pressure. In a low concentration range, the sample containing the *Typhula ishikariensis*-originated antifreeze protein is exhibited approximately the same freezing point as that of the sample containing the fish-originated antifreeze protein (Type III). In a concentration of 10 mg/ml or more, the sample containing the fish-originated antifreeze protein (Type III) had a constant freezing point of about −0.73° C., whereas the sample containing the *Typhula ishikariensis*-originated antifreeze protein showed a certain freezing point depression in the concentration of 10 to 20 mg/ml, and the lowest value was −0.96° C. The result is shown FIG. 2 as the difference between the freezing point and the melting point, or freezing point depression.

The above test result proves that the antifreeze protein of the present invention provides a greater thermal hysteresis and a higher antifreeze activity than those in the conventional antifreeze protein.

Example 5

Cloning *Typhula ishikariensis*-Originated Antifreeze Protein mRNA was extracted from 1 g of *Typhula ishikariensis* cells cultured at 0° C. or less for one month by using a RNA adjustment kit (available from QIAGEN). Based on the obtained mRNA, cDNA and cDNA library were prepared by using a cDNA preparation kit (BD Bioscience Clontech).

Then, N-terminal and internal amino acid sequences of a purified *Typhula ishikariensis*-originated antifreeze protein, and a *Typhula ishikariensis*-originated antifreeze protein peptide obtained through trypsin treatment, were determined by using a protein sequencer (available from Applied Biosystem). Based on the obtained sequences, a specific primer of the *Typhula ishikariensis*-originated antifreeze protein was prepared. A part of the DNA of the antifreeze protein was amplified through PCR reaction with the cDNA template by using the designed specific primer of the *Typhula ishikariensis*-originated antifreeze protein, and a fragment of the amplified region was isolated. Further, the polynucleotides encoding the antifreeze proteins of the present invention were isolated from the cDNA library through a 3'/5'-RACE method in their entire length. By checking with the Protein Sequence Database, it was verified that all of seven, isolated polynucleotides encoding antifreeze proteins were novel. The base sequences of the seven polynucleotides are shown in SEQ ID NOS: 8, 10, 12, 14, 16, 18 and 20, respectively. The amino acid sequences of proteins encoded by the polynucleotides are shown in SEQ ID NOS: 9, 11, 13, 15, 17, 19 and 21, respectively.

Example 6

Preparation of *Typhula ishikariensis*-Originated Antifreeze Protein Using Yeast Expression System The polynucleotide encoding a *Typhula ishikariensis*-originated antifreeze protein obtained through cloning was inserted into the chromosome of methylotrophic yeast (*Pichia partoris*) by using a methylotrophic yeast expression system preparation kit (available from INVITROGEN). When the obtained methylotrophic yeast transformant was cultured in BMMY medium at 25° C. for five days, the *Typhula ishikariensis*-originated antifreeze protein was excreted in the medium. A sample was taken from the medium to check the ice crystal configuration therein. As a result, a specific star-shaped ice crystal was observed in the antifreeze protein. This means that the *Typhula ishikariensis*-originated antifreeze protein prepared through the gene recombination method exhibits a sufficient antifreeze activity.

As mentioned above, the antifreeze protein originated from basidiomycetes has a higher antifreeze activity, such as a thermal hysteresis activity or an ice-recrystallization inhibition activity, as compared to the conventional antifreeze proteins. In addition, by taking advantage of biological properties of fungi, the antifreeze protein of the present invention can be readily cultured and prepared in large quantities at a low cost. It is believed that the antifreeze protein of the present invention has a high level of safety because no toxicity to human in all of the tested basidiomycetes has been reported. Thus, the present invention provides a significantly useful and valuable technology for facilitating the utilization of antifreeze proteins as a quality improving agent for frozen foods such as ice cream, a cryopreservative for cells, or an additive for eliminating clogging of pipelines due to freeze in cryogenic supply systems or cryogenic storage systems.

What is claimed is:

1. An isolated or recombinant protein having the amino acid sequence of SEQ ID NO:9, wherein said protein depresses the freezing point of an aqueous solution.

2. An isolated or recombinant protein having an amino acid sequence at least 95% identical to the amino acid sequence of SEQ ID NO:9, and wherein said protein depresses the freezing point of an aqueous solution.

3. An isolated or recombinant protein comprising the amino acid residues 21-243 of SEQ ID NO:9, wherein said protein depresses the freezing point of an aqueous solution.

4. An isolated or recombinant protein having an amino acid sequence at least 95% identical to the amino acid residues 21-243 of SEQ ID NO:9, and wherein said protein depresses the freezing point of an aqueous solution.

* * * * *

SEQUENCE LISTING

```
<160> NUMBER OF SEQ ID NOS: 21

<210> SEQ ID NO 1
<211> LENGTH: 20
<212> TYPE: PRT
<213> ORGANISM: Typhula ishikariensis

<400> SEQUENCE: 1

Ala Gly Pro Ser Ala Val Ala Gly Leu Thr Ala Gly Asn Tyr Ala Ile
1               5                   10                  15

Leu Ala Ser Thr
            20
```

```
<210> SEQ ID NO 2
<211> LENGTH: 20
<212> TYPE: PRT
<213> ORGANISM: Typhula ishikariensis

<400> SEQUENCE: 2

Ala Gly Pro Ser Ala Val Pro Leu Gly Thr Ala Gly Asn Tyr Val Ile
1               5                   10                  15

Leu Ala Ser Thr
            20

<210> SEQ ID NO 3
<211> LENGTH: 20
<212> TYPE: PRT
<213> ORGANISM: Typhula ishikariensis

<400> SEQUENCE: 3

Ala Gly Pro Thr Ala Val Pro Leu Gly Thr Ala Gly Asn Tyr Ala Ile
1               5                   10                  15

Leu Ala Ser Thr
            20

<210> SEQ ID NO 4
<211> LENGTH: 20
<212> TYPE: PRT
<213> ORGANISM: Typhula ishikariensis

<400> SEQUENCE: 4

Ala Gly Pro Ser Ala Val Pro Leu Gly Thr Ala Gly Asn Tyr Ala Ile
1               5                   10                  15

Leu Ala Ser Thr
            20

<210> SEQ ID NO 5
<211> LENGTH: 20
<212> TYPE: PRT
<213> ORGANISM: Coprinus psychromorbidus

<400> SEQUENCE: 5

Ala Gly Pro Thr Ala Val Asn Leu Gly Thr Ala Lys Asn Tyr Ala Ile
1               5                   10                  15

Leu Thr Lys Ala
            20

<210> SEQ ID NO 6
<211> LENGTH: 20
<212> TYPE: PRT
<213> ORGANISM: Coprinus psychromorbidus

<400> SEQUENCE: 6

Ala Gly Pro Thr Ala Val Asn Leu Gly Thr Ala Lys Thr Tyr Ala Ile
1               5                   10                  15

Leu Thr Lys Ala
            20

<210> SEQ ID NO 7
<211> LENGTH: 20
<212> TYPE: PRT
<213> ORGANISM: Coprinus psychromorbidus

<400> SEQUENCE: 7
```

-continued

```
Ala Gly Pro Thr Ala Val Asn Leu Gly Thr Ala Lys Asn Tyr Ala Ile
1               5                   10                  15

Leu Thr Lys Thr
            20

<210> SEQ ID NO 8
<211> LENGTH: 732
<212> TYPE: DNA
<213> ORGANISM: Typhula ishikariensis
<400> SEQUENCE: 8
atgttctcct caacctacct cctcgcaatc atcgccttgg ctgtctcaag cgtttttgct     60
gctggtccca ccgctgtccc ccttggaacc gccggcaact acgccattct cgcgtcggct    120
ggcgtttcga ctgtccccca gtctgtcatc actggtgccg tcggactttc ccccgctgct    180
gcgactttcc tcaccggatt tagtctcacg atgtctagca ccggcacctt ttccacgtca    240
actcaagtca ctggccagct tactgctgct gactatggta cgcctacccc tagtattttg    300
accactgcga tcggcgacat gggaactgcc tatgtcaacg cagctactcg atcgggaccc    360
aactttctcg agatttacac tggggcactt ggcgggaaga ttctccctcc tggtctatac    420
aaatggactt ctcccgtcgg tgcctccgct gacttcacca ttattggtac atccaccgac    480
acctggatct tccaaattgc tgggactctt ggactcgccg ctggaaagaa aatcatcctt    540
gctggtggag ctcaggctaa gaacatcgtc tgggttgttg ctggcgctgt ctccatcgaa    600
gctggagcca agtttgaggg tgttatcctc gcaaaaactg ccgttaccct caagaccgga    660
tcctccctca acggaaggat tttgtcgcag actgccgttg ccttgcaaaa ggctaccgtc    720
gtgcaaaagt ag                                                        732

<210> SEQ ID NO 9
<211> LENGTH: 243
<212> TYPE: PRT
<213> ORGANISM: Typhula ishikariensis
<400> SEQUENCE: 9

Met Phe Ser Ser Thr Tyr Leu Leu Ala Ile Ile Ala Leu Ala Val Ser
1               5                   10                  15

Ser Val Phe Ala Ala Gly Pro Thr Ala Val Pro Leu Gly Thr Ala Gly
            20                  25                  30

Asn Tyr Ala Ile Leu Ala Ser Ala Gly Val Ser Thr Val Pro Gln Ser
        35                  40                  45

Val Ile Thr Gly Ala Val Gly Leu Ser Pro Ala Ala Ala Thr Phe Leu
    50                  55                  60

Thr Gly Phe Ser Leu Thr Met Ser Ser Thr Gly Thr Phe Ser Thr Ser
65                  70                  75                  80

Thr Gln Val Thr Gly Gln Leu Thr Ala Ala Asp Tyr Gly Thr Pro Thr
                85                  90                  95

Pro Ser Ile Leu Thr Thr Ala Ile Gly Asp Met Gly Thr Ala Tyr Val
            100                 105                 110

Asn Ala Ala Thr Arg Ser Gly Pro Asn Phe Leu Glu Ile Tyr Thr Gly
        115                 120                 125

Ala Leu Gly Gly Lys Ile Leu Pro Pro Gly Leu Tyr Lys Trp Thr Ser
    130                 135                 140

Pro Val Gly Ala Ser Ala Asp Phe Thr Ile Ile Gly Thr Ser Thr Asp
145                 150                 155                 160

Thr Trp Ile Phe Gln Ile Ala Gly Thr Leu Gly Leu Ala Ala Gly Lys
```

```
                165                 170                 175
Lys Ile Ile Leu Ala Gly Gly Ala Gln Ala Lys Asn Ile Val Trp Val
            180                 185                 190

Val Ala Gly Ala Val Ser Ile Glu Ala Gly Ala Lys Phe Glu Gly Val
            195                 200                 205

Ile Leu Ala Lys Thr Ala Val Thr Leu Lys Thr Gly Ser Ser Leu Asn
            210                 215                 220

Gly Arg Ile Leu Ser Gln Thr Ala Val Ala Leu Gln Lys Ala Thr Val
225                 230                 235                 240

Val Gln Lys

<210> SEQ ID NO 10
<211> LENGTH: 732
<212> TYPE: DNA
<213> ORGANISM: Typhula ishikariensis

<400> SEQUENCE: 10
atgttctccg catcctccct tctcgctgtt attgcgttgg ctatctccag cgtctctgcc      60
gctggtccct ctgctgtccc actcggaact gcgggaaact atgttattct cgcgtcgact     120
ggcgtttcga ctgtccccca gtctgtcatc actggcgccg tcggagtctc tcccggtact     180
gccgcttccc ttaccggctt cagccttata ctatctggca ccggcacctt ctccacgtcg     240
tctcaggtca ctggccagct tactggtgcc gactacggga cgcctactcc tagtattttg     300
accactgcga ttggcgacat gggaactgcc tatattaacg cagctactcg atcgggaccc     360
gacttcctcg agatttacac tggggcgctt ggcgggacga ctctccttcc tggtctatac     420
aagtggaccc ttccgttgg tgcctccgcc gactttacca ttagtggcac atccaccgac     480
acatggattt tccagattga cggcactctt gatgttgcaa ctgggaagca gatcactctc     540
gttggcggag ctcaggctaa gaacatcatc tgggtcgtag ctggagctgt taacattgag     600
gttggggcaa agttcgaagg gaccatcctc gcaaaaactg ccgtcacctt caagaccggt     660
tcatccctca acggaaggat tctggcgcag acttctgtcg ctctgcagtc cgctaccatt     720
gtggaaaagt ag                                                         732

<210> SEQ ID NO 11
<211> LENGTH: 243
<212> TYPE: PRT
<213> ORGANISM: Typhula ishikariensis

<400> SEQUENCE: 11

Met Phe Ser Ala Ser Ser Leu Leu Ala Val Ile Ala Leu Ala Ile Ser
1               5                   10                  15

Ser Val Ser Ala Ala Gly Pro Ser Ala Val Pro Leu Gly Thr Ala Gly
            20                  25                  30

Asn Tyr Val Ile Leu Ala Ser Thr Gly Val Ser Thr Val Pro Gln Ser
            35                  40                  45

Val Ile Thr Gly Ala Val Gly Val Ser Pro Gly Thr Ala Ala Ser Leu
    50                  55                  60

Thr Gly Phe Ser Leu Ile Leu Ser Gly Thr Gly Thr Phe Ser Thr Ser
65                  70                  75                  80

Ser Gln Val Thr Gly Gln Leu Thr Gly Ala Asp Tyr Gly Thr Pro Thr
            85                  90                  95

Pro Ser Ile Leu Thr Thr Ala Ile Gly Asp Met Gly Thr Ala Tyr Ile
            100                 105                 110
```

```
Asn Ala Ala Thr Arg Ser Gly Pro Asp Phe Leu Glu Ile Tyr Thr Gly
        115                 120                 125

Ala Leu Gly Gly Thr Thr Leu Leu Pro Gly Leu Tyr Lys Trp Thr Ser
    130                 135                 140

Ser Val Gly Ala Ser Ala Asp Phe Thr Ile Ser Gly Thr Ser Thr Asp
145                 150                 155                 160

Thr Trp Ile Phe Gln Ile Asp Gly Thr Leu Asp Val Ala Thr Gly Lys
                165                 170                 175

Gln Ile Thr Leu Val Gly Gly Ala Gln Ala Lys Asn Ile Ile Trp Val
            180                 185                 190

Val Ala Gly Ala Val Asn Ile Glu Val Gly Ala Lys Phe Glu Gly Thr
        195                 200                 205

Ile Leu Ala Lys Thr Ala Val Thr Phe Lys Thr Gly Ser Ser Leu Asn
    210                 215                 220

Gly Arg Ile Leu Ala Gln Thr Ser Val Ala Leu Gln Ser Ala Thr Ile
225                 230                 235                 240

Val Glu Lys

<210> SEQ ID NO 12
<211> LENGTH: 732
<212> TYPE: DNA
<213> ORGANISM: Typhula ishikariensis

<400> SEQUENCE: 12
atgttctccg catcctccct tctcgctgtt attgcgttgg ctgtctccag cgtctctgcc      60
gctggtccct ctgctgtccc actcggaact gcgggaaact atgttattct cgcgtcgact     120
ggcgtttcga ctgtccccca gtctgtcatc actggcgccg tcggagtctc tcccggtact     180
gccgcttccc ttaccggctt cagccttata ctatctggca ccggcacctt ctccacgtcg     240
tctcaggtca ctggccagct tactggtgcc gactacggga cgcctactcc tagtattttg     300
accactgcga ttggcgacat gggaactgcc tatattaacg cagctactcg atcgggaccc     360
gacttcctcg agatttacac tggtgcgctt ggcgggacga ctctccttcc tggtctatac     420
aagtggacct cttccgttgg tgcctccgcc gactttacca ttagtggcac atccaccgac     480
acatggattt tccagattga cggcactctt gatgttgcaa ctgggaagca gatcactctc     540
gttggcggag ctcaggctaa gaacatcatc tgggttgtag ctggagctgt taacattgag     600
gttgggcaa agttcgaagg gaccatcctc gcaaaaactg ccgtcacctt caagaccggt     660
tcatccctca acggaaggat tctggcgcag actgctgtcg ctctgcagtc cgctaccatt     720
gtggaaaagt ag                                                         732

<210> SEQ ID NO 13
<211> LENGTH: 243
<212> TYPE: PRT
<213> ORGANISM: Typhula ishikariensis

<400> SEQUENCE: 13

Met Phe Ser Ala Ser Ser Leu Leu Ala Val Ile Ala Leu Ala Val Ser
1               5                   10                  15

Ser Val Ser Ala Ala Gly Pro Ser Ala Val Pro Leu Gly Thr Ala Gly
            20                  25                  30

Asn Tyr Val Ile Leu Ala Ser Thr Gly Val Ser Thr Val Pro Gln Ser
        35                  40                  45

Val Ile Thr Gly Ala Val Gly Val Ser Pro Gly Thr Ala Ala Ser Leu
    50                  55                  60
```

Thr Gly Phe Ser Leu Ile Leu Ser Gly Thr Gly Thr Phe Ser Thr Ser
65                  70                  75                  80

Ser Gln Val Thr Gly Gln Leu Thr Gly Ala Asp Tyr Gly Thr Pro Thr
                85                  90                  95

Pro Ser Ile Leu Thr Thr Ala Ile Gly Asp Met Gly Thr Ala Tyr Ile
            100                 105                 110

Asn Ala Ala Thr Arg Ser Gly Pro Asp Phe Leu Glu Ile Tyr Thr Gly
        115                 120                 125

Ala Leu Gly Gly Thr Thr Leu Leu Pro Gly Leu Tyr Lys Trp Thr Ser
    130                 135                 140

Ser Val Gly Ala Ser Ala Asp Phe Thr Ile Ser Gly Thr Ser Thr Asp
145                 150                 155                 160

Thr Trp Ile Phe Gln Ile Asp Gly Thr Leu Asp Val Ala Thr Gly Lys
                165                 170                 175

Gln Ile Thr Leu Val Gly Gly Ala Gln Ala Lys Asn Ile Ile Trp Val
            180                 185                 190

Val Ala Gly Ala Val Asn Ile Glu Val Gly Ala Lys Phe Glu Gly Thr
        195                 200                 205

Ile Leu Ala Lys Thr Ala Val Thr Phe Lys Thr Gly Ser Ser Leu Asn
    210                 215                 220

Gly Arg Ile Leu Ala Gln Thr Ala Val Ala Leu Gln Ser Ala Thr Ile
225                 230                 235                 240

Val Glu Lys

<210> SEQ ID NO 14
<211> LENGTH: 732
<212> TYPE: DNA
<213> ORGANISM: Typhula ishikariensis

<400> SEQUENCE: 14
atgttctccg catcctccct tctcgctgtt attgcgttgg ctgtctccag cgtctctgcc      60
gctggtccct ctgctgtccc actcggaact gcgggaaact atgttattct cgcgtcgact     120
ggcgtttcga ctgtccccca gtctgtcatc actggcgccg tcggagtctc tcccggtact     180
gccgcttccc ttaccggctt cagccttata ctatctggca ccggcacctt ctccacgtcg     240
tctcaggtca ctggccagct tactggtgcc gactacggga cgcctactcc tagtattttg     300
accactgcga ttggcgacat gggaactgcc tatattaacg cagctactcg atcgggaccc     360
gacttcctcg agatttacac tggtgcgctt ggcgggacga ctctccttcc tggtctatac     420
aagtggacct cttccgttgg tgcctccgcc gactttacca ttagtggcac atccaccgac     480
acatggattt tccagattga cggcactctt gatgttgcaa ctgggaagca gatcactctc     540
gttggcggag ctcaggctaa gaacatcatc tgggttgtag ctggagctgt aacattgag     600 gttgggcaa agttcgaagg gaccatcctc gcaaaaactg ccgtcacctt caagaccggt     660
tcatccctca acggaaggat tctggcgcag actgctgtcg ctctgcagtc cgcgtccatt     720
gtggaaaagt ag                                                         732

<210> SEQ ID NO 15
<211> LENGTH: 243
<212> TYPE: PRT
<213> ORGANISM: Typhula ishikariensis

<400> SEQUENCE: 15

Met Phe Ser Ala Ser Ser Leu Leu Ala Val Ile Ala Leu Ala Val Ser

```
              1               5                  10                 15
         Ser Val Ser Ala Ala Gly Pro Ser Ala Val Pro Leu Gly Thr Ala Gly
                          20                  25                  30

Asn Tyr Val Ile Leu Ala Ser Thr Gly Val Ser Thr Val Pro Gln Ser
                      35                  40                  45

Val Ile Thr Gly Ala Val Gly Val Ser Pro Gly Thr Ala Ala Ser Leu
              50                  55                  60

Thr Gly Phe Ser Leu Ile Leu Ser Gly Thr Gly Thr Phe Ser Thr Ser
         65                  70                  75                  80

Ser Gln Val Thr Gly Gln Leu Thr Gly Ala Asp Tyr Gly Thr Pro Thr
                          85                  90                  95

Pro Ser Ile Leu Thr Thr Ala Ile Gly Asp Met Gly Thr Ala Tyr Ile
                      100                 105                 110

Asn Ala Ala Thr Arg Ser Gly Pro Asp Phe Leu Glu Ile Tyr Thr Gly
                      115                 120                 125

Ala Leu Gly Gly Thr Thr Leu Leu Pro Gly Leu Tyr Lys Trp Thr Ser
              130                 135                 140

Ser Val Gly Ala Ser Ala Asp Phe Thr Ile Ser Gly Thr Ser Thr Asp
         145                 150                 155                 160

Thr Trp Ile Phe Gln Ile Asp Gly Thr Leu Asp Val Ala Thr Gly Lys
                          165                 170                 175

Gln Ile Thr Leu Val Gly Gly Ala Gln Ala Lys Asn Ile Ile Trp Val
                      180                 185                 190

Val Ala Gly Ala Val Asn Ile Glu Val Gly Ala Lys Phe Glu Gly Thr
              195                 200                 205

Ile Leu Ala Lys Thr Ala Val Thr Phe Lys Thr Gly Ser Ser Leu Asn
         210                 215                 220

Gly Arg Ile Leu Ala Gln Thr Ala Val Ala Leu Gln Ser Ala Ser Ile
         225                 230                 235                 240

Val Glu Lys

<210> SEQ ID NO 16
         <211> LENGTH: 732
         <212> TYPE: DNA
         <213> ORGANISM: Typhula ishikariensis

<400> SEQUENCE: 16
atgttctcct caacctacct cctcgcaatc atcgccttgg ctatctcaag cgtttctgct    60
gctggaccca ccgctgtccc ccttggaacc gccggcaact acgccatcct cgcgtcgacc   120 gctgttttcca ccgtccccca gtctgccatt actggtgccg tcggaatttc ccccgctgct   180
gggactttcc ttaccggatt tagtctcacg atgtctggca ccggcacctt ttccacgtca   240
actcaagtca ccggccagct tactgctgct gactacggga cgcctacccc tagtattta    300 accactgcga ttggcgacat gggaactgcc tataccaacg gagctactcg atcgggaccc   360
gacttcctcg agatttacac tggggcgctt ggcgggacga ctctccttcc tggtctatac   420
aagtggacct cttccgttgg tgcctccgcc gactttacca ttagtggcac atccaccgac   480
acatggattt tccaaattga cggcactctt ggactcgccg ccggaaagaa aatcacccct   540
gctggcggag ctcaggctaa gaacatcatc tgggttgtag ctggagctgt tagcattgag   600
gctggagccc agttcgaggg tgttatcctc gcaaaaactg ccgttactct caagaccgga   660
tcctccctca acggaaggat tttggcgcag acttctgttg ctctgcagtc cgctaccgtc   720
gtgcaaaagt ag                                                       732
```

<210> SEQ ID NO 17
<211> LENGTH: 243
<212> TYPE: PRT
<213> ORGANISM: Typhula ishikariensis

<400> SEQUENCE: 17

```
Met Phe Ser Ser Thr Tyr Leu Leu Ala Ile Ile Ala Leu Ala Ile Ser
1               5                   10                  15

Ser Val Ser Ala Ala Gly Pro Thr Ala Val Pro Leu Gly Thr Ala Gly
            20                  25                  30

Asn Tyr Ala Ile Leu Ala Ser Thr Ala Val Ser Thr Val Pro Gln Ser
        35                  40                  45

Ala Ile Thr Gly Ala Val Gly Ile Ser Pro Ala Ala Gly Thr Phe Leu
    50                  55                  60

Thr Gly Phe Ser Leu Thr Met Ser Gly Thr Gly Thr Phe Ser Thr Ser
65                  70                  75                  80

Thr Gln Val Thr Gly Gln Leu Thr Ala Ala Asp Tyr Gly Thr Pro Thr
                85                  90                  95

Pro Ser Ile Leu Thr Thr Ala Ile Gly Asp Met Gly Thr Ala Tyr Thr
            100                 105                 110

Asn Gly Ala Thr Arg Ser Gly Pro Asp Phe Leu Glu Ile Tyr Thr Gly
        115                 120                 125

Ala Leu Gly Gly Thr Thr Leu Leu Pro Gly Leu Tyr Lys Trp Thr Ser
    130                 135                 140

Ser Val Gly Ala Ser Ala Asp Phe Thr Ile Ser Gly Thr Ser Thr Asp
145                 150                 155                 160

Thr Trp Ile Phe Gln Ile Asp Gly Thr Leu Gly Leu Ala Ala Gly Lys
                165                 170                 175

Lys Ile Thr Leu Ala Gly Gly Ala Gln Ala Lys Asn Ile Ile Trp Val
            180                 185                 190

Val Ala Gly Ala Val Ser Ile Glu Ala Gly Ala Gln Phe Glu Gly Val
        195                 200                 205

Ile Leu Ala Lys Thr Ala Val Thr Leu Lys Thr Gly Ser Ser Leu Asn
    210                 215                 220

Gly Arg Ile Leu Ala Gln Thr Ser Val Ala Leu Gln Ser Ala Thr Val
225                 230                 235                 240

Val Gln Lys
```

<210> SEQ ID NO 18
<211> LENGTH: 732
<212> TYPE: DNA
<213> ORGANISM: Typhula ishikariensis

<400> SEQUENCE: 18

```
atgttctccg catcctccct tctcgctgtt attgcgttga ctatctccag cgtctctgcc    60
gctggtccct ctgctgtccc actcggaact gcgggaaact atgttattct cgcgtcgact   120
ggcgtttcga ctgtcccccca gtctgtcatc actggcgccg tcggagtctc tcccggtact   180
gccgcttccc ttaccggctt cagccttata ctatctggca ccggcacctt ctccacgtcg   240
tctcaggtca ctggccagct tactggtgcc gactacggga cgcctactcc tagtattttg   300
accactgcga ttggcgacat gggaactgcc tatattaacg cagctactcg atcgggaccc   360
gacttcctcg agatttacac tggggcgctt ggcgggacga ctctccttcc tggtctatac   420
aagtggacct cttccgttgg tgcctccgcc gactttacca ttagtggcac atccaccgac   480
```

-continued

```
acatggattt tccagattga cggcactctt gatgttgcaa ctgggaagca gatcactctc    540
gttggcggag ctcaggctaa gaacgtcatc tgggttgtag ctggagctgt taacattgag    600 gttgggcaa agttcgaagg gaccatcctc gcaaaaactg ccgtcacctt caagaccggt    660
tcatccctca acggaaggat tctggcgcag actgctgtcg ctctgcagtc cgctaccatt    720
gtggaaaagt ag                                                       732
```

<210> SEQ ID NO 19
<211> LENGTH: 243
<212> TYPE: PRT
<213> ORGANISM: Typhula ishikariensis

<400> SEQUENCE: 19

```
Met Phe Ser Ala Ser Ser Leu Leu Ala Val Ile Ala Leu Thr Ile Ser
1               5                   10                  15

Ser Val Ser Ala Ala Gly Pro Ser Ala Val Pro Leu Gly Thr Ala Gly
            20                  25                  30

Asn Tyr Val Ile Leu Ala Ser Thr Gly Val Ser Thr Val Pro Gln Ser
        35                  40                  45

Val Ile Thr Gly Ala Val Gly Val Ser Pro Gly Thr Ala Ala Ser Leu
    50                  55                  60

Thr Gly Phe Ser Leu Ile Leu Ser Gly Thr Gly Thr Phe Ser Thr Ser
65                  70                  75                  80

Ser Gln Val Thr Gly Gln Leu Thr Gly Ala Asp Tyr Gly Thr Pro Thr
                85                  90                  95

Pro Ser Ile Leu Thr Thr Ala Ile Gly Asp Met Gly Thr Ala Tyr Ile
            100                 105                 110

Asn Ala Ala Thr Arg Ser Gly Pro Asp Phe Leu Glu Ile Tyr Thr Gly
        115                 120                 125

Ala Leu Gly Gly Thr Thr Leu Leu Pro Gly Leu Tyr Lys Trp Thr Ser
    130                 135                 140

Ser Val Gly Ala Ser Ala Asp Phe Thr Ile Ser Gly Thr Ser Thr Asp
145                 150                 155                 160

Thr Trp Ile Phe Gln Ile Asp Gly Thr Leu Asp Val Ala Thr Gly Lys
                165                 170                 175

Gln Ile Thr Leu Val Gly Gly Ala Gln Ala Lys Asn Val Ile Trp Val
            180                 185                 190

Val Ala Gly Ala Val Asn Ile Glu Val Gly Ala Lys Phe Glu Gly Thr
        195                 200                 205

Ile Leu Ala Lys Thr Ala Val Thr Phe Lys Thr Gly Ser Ser Leu Asn
    210                 215                 220

Gly Arg Ile Leu Ala Gln Thr Ala Val Ala Leu Gln Ser Ala Thr Ile
225                 230                 235                 240

Val Glu Lys
```

<210> SEQ ID NO 20
<211> LENGTH: 732
<212> TYPE: DNA
<213> ORGANISM: Typhula ishikariensis

<400> SEQUENCE: 20

```
atgttctccg catcctccct tctcgctgtt attgcgttgg ctatctccag cgtctctgcc     60
gctggtccct ctgctgtccc actcggaact gcgggaaact atgttattct cgcgtcgact    120
ggcgtttcga ctgtccccca gtctgtcatc actggcgccg tcggagtctc tcccggtact    180
```

-continued

```
gccgcttccc ttaccggctt cagccttata ctatctggca ccggcacctt ctccacgtcg      240
tctcaggtca ctggccagct tactggtgct gactacggga cgcctactcc tagtattttg      300
accactgcga ttggcgacat gggaactgcc tatattaacg cagctactcg atcgggaccc      360
gacttcctcg agatttacac tggggcgctt ggcgggacga ctctccttcc tggtctatac      420
aagtggacct cttccgttgg tgcctccgcc gactttacca ttagtggcac atccaccgac      480
acatggattt tccaaattga cggcactctt ggactcgccg ccggaaagaa aatcactctc      540
gttggcggag ctcaggctaa gaacgtcatc tgggttgtag ctggagctgt taacattgag      600 gttgggcaa agttcgaagg gaccatcctc gcaaaaactg ccgtcacctt caagaccggt       660
tcatccctca acggaaggat tctggcgcag actgctgtcg ctctgcagtc cgctaccatt      720
gtggaaaagt ag                                                          732
```

<210> SEQ ID NO 21
<211> LENGTH: 243
<212> TYPE: PRT
<213> ORGANISM: Typhula ishikariensis

<400> SEQUENCE: 21

```
Met Phe Ser Ala Ser Ser Leu Leu Ala Val Ile Ala Leu Ala Ile Ser
1               5                   10                  15

Ser Val Ser Ala Ala Gly Pro Ser Ala Val Pro Leu Gly Thr Ala Gly
                20                  25                  30

Asn Tyr Val Ile Leu Ala Ser Thr Gly Val Ser Thr Val Pro Gln Ser
            35                  40                  45

Val Ile Thr Gly Ala Val Gly Val Ser Pro Gly Thr Ala Ala Ser Leu
        50                  55                  60

Thr Gly Phe Ser Leu Ile Leu Ser Gly Thr Gly Thr Phe Ser Thr Ser
65                  70                  75                  80

Ser Gln Val Thr Gly Gln Leu Thr Gly Ala Asp Tyr Gly Thr Pro Thr
                85                  90                  95

Pro Ser Ile Leu Thr Thr Ala Ile Gly Asp Met Gly Thr Ala Tyr Ile
                100                 105                 110

Asn Ala Ala Thr Arg Ser Gly Pro Asp Phe Leu Glu Ile Tyr Thr Gly
            115                 120                 125

Ala Leu Gly Gly Thr Thr Leu Leu Pro Gly Leu Tyr Lys Trp Thr Ser
        130                 135                 140

Ser Val Gly Ala Ser Ala Asp Phe Thr Ile Ser Gly Thr Ser Thr Asp
145                 150                 155                 160

Thr Trp Ile Phe Gln Ile Asp Gly Thr Leu Gly Leu Ala Ala Gly Lys
                165                 170                 175

Lys Ile Thr Leu Val Gly Gly Ala Gln Ala Lys Asn Val Ile Trp Val
            180                 185                 190

Val Ala Gly Ala Val Asn Ile Glu Val Gly Ala Lys Phe Glu Gly Thr
        195                 200                 205

Ile Leu Ala Lys Thr Ala Val Thr Phe Lys Thr Gly Ser Ser Leu Asn
    210                 215                 220

Gly Arg Ile Leu Ala Gln Thr Ala Val Ala Leu Gln Ser Ala Thr Ile
225                 230                 235                 240

Val Glu Lys
```